(12) United States Patent
Helgerson et al.

(10) Patent No.: US 8,529,609 B2
(45) Date of Patent: Sep. 10, 2013

(54) POLYAXIAL FACET FIXATION SCREW SYSTEM

(75) Inventors: Joel R. Helgerson, Erie, CO (US); Shresta Marigowda, Morton, PA (US); Andrew Fauth, River Heights, UT (US)

(73) Assignee: OsteoMed LLC, Addison, TX (US)

(*) Notice: Subject to any disclaimer, the term of this patent is extended or adjusted under 35 U.S.C. 154(b) by 217 days.

(21) Appl. No.: 12/957,056

(22) Filed: Nov. 30, 2010

(65) Prior Publication Data

US 2011/0182693 A1    Jul. 28, 2011

Related U.S. Application Data

(60) Provisional application No. 61/265,614, filed on Dec. 1, 2009, provisional application No. 61/374,862, filed on Aug. 18, 2010.

(51) Int. Cl.
*A61B 17/86* (2006.01)

(52) U.S. Cl.
USPC .......... 606/306; 606/301; 606/328; 606/290; 606/247

(58) Field of Classification Search
USPC ............... 606/247, 266–269, 272, 289–291, 606/293–296, 301, 302, 305–308, 319, 328, 606/320, 322; 411/533, 537, 911, 132, 141, 411/142; 192/44, 64; 81/59.1
See application file for complete search history.

(56) References Cited

U.S. PATENT DOCUMENTS

| | | | | |
|---|---|---|---|---|
| 1,155,844 A | * | 10/1915 | Smith | 411/132 |
| 1,391,186 A | * | 9/1921 | Hill | 411/132 |
| 1,609,645 A | * | 12/1926 | Dewire | 411/396 |
| 1,627,404 A | * | 5/1927 | Outhier | 411/298 |
| 1,792,381 A | * | 2/1931 | Lescadieu | 411/298 |
| 3,181,584 A | * | 5/1965 | Borowsky | 411/134 |
| 4,290,328 A | | 9/1981 | Clark | |
| 5,125,489 A | * | 6/1992 | Cha | 192/64 |
| 5,261,909 A | | 11/1993 | Sutterlin | |
| 5,527,312 A | | 6/1996 | Ray | |
| 5,611,800 A | | 3/1997 | Davis | |
| 6,148,696 A | | 11/2000 | Chiang | |
| 6,227,782 B1 | * | 5/2001 | Bowling et al. | 411/114 |
| 6,248,108 B1 | * | 6/2001 | Tormala et al. | 606/318 |
| 6,443,987 B1 | | 9/2002 | Bryan | |

(Continued)

FOREIGN PATENT DOCUMENTS

EP    0932367 B1    11/2003
WO    WO2004019757 A2    3/2004

(Continued)

OTHER PUBLICATIONS

Grob; *Translaminar Screw Fixation in the Lumbar Spine:* Technique, Indications. European Spine Journal, 1987: 7 pp. 178-186.

(Continued)

*Primary Examiner* — Michael T Schaper
(74) *Attorney, Agent, or Firm* — Fulbright & Jaworski LLP

(57) ABSTRACT

A screw system includes a screw and a washer assembly captive to the screw. The washer assembly is polyaxially pivotable relative to the screw. The screw may be freely rotated in one direction relative to the washer assembly, but frictionally binds with the washer assembly when rotated in a second direction.

22 Claims, 8 Drawing Sheets

(56) References Cited

U.S. PATENT DOCUMENTS

| | | | |
|---|---|---|---|
| 6,485,518 B1 | 11/2002 | Cornwall | |
| 6,502,679 B1* | 1/2003 | Wang | 192/64 |
| 6,565,573 B1 | 5/2003 | Ferrante | |
| 7,060,068 B2 | 6/2006 | Tromanhauser | |
| 7,294,128 B2 | 11/2007 | Alleyne | |
| 7,396,360 B2 | 7/2008 | Lieberman | |
| 7,522,953 B2 | 4/2009 | Kaula | |
| 7,563,275 B2 | 7/2009 | Falahee | |
| 7,575,343 B2 | 8/2009 | Li | |
| 7,708,761 B2 | 5/2010 | Petersen | |
| 7,824,429 B2 | 11/2010 | Culbert | |
| 2003/0077143 A1* | 4/2003 | Smolarek | 411/161 |
| 2005/0228386 A1 | 10/2005 | Ziolo et al. | |
| 2006/0074425 A1 | 4/2006 | Sutterlin | |
| 2006/0111779 A1 | 5/2006 | Petersen | |
| 2006/0217713 A1* | 9/2006 | Serhan et al. | 606/61 |
| 2006/0217715 A1* | 9/2006 | Serhan et al. | 606/61 |
| 2006/0235391 A1 | 10/2006 | Sutterlin | |
| 2008/0021480 A1 | 1/2008 | Chin | |
| 2008/0147079 A1 | 6/2008 | Chin | |
| 2008/0255622 A1 | 10/2008 | Mickiewicz | |
| 2009/0054903 A1 | 2/2009 | Falahee | |
| 2009/0076551 A1 | 3/2009 | Petersen | |
| 2009/0099602 A1 | 4/2009 | Aflatoon | |
| 2009/0192551 A1 | 7/2009 | Cianfrani et al. | |
| 2009/0234397 A1 | 9/2009 | Petersen | |
| 2009/0312798 A1 | 12/2009 | Varela | |
| 2009/0312800 A1 | 12/2009 | Chin | |
| 2010/0174324 A1* | 7/2010 | Derouet | 606/305 |
| 2010/0222829 A1 | 9/2010 | Petersen | |

FOREIGN PATENT DOCUMENTS

| | | | |
|---|---|---|---|
| WO | WO2006017507 A2 | 2/2006 | |
| WO | WO2006057943 A2 | 6/2006 | |
| WO | WO2007070819 A2 | 6/2007 | |
| WO | WO2007084900 A2 | 7/2007 | |
| WO | WO2007109402 A2 | 9/2007 | |
| WO | WO2007120903 A2 | 10/2007 | |
| WO | WO2007127610 A1 | 11/2007 | |
| WO | WO2007127687 A2 | 11/2007 | |
| WO | WO2007143709 A2 | 12/2007 | |
| WO | WO2008086533 A2 | 7/2008 | |
| WO | WO2008106240 A2 | 9/2008 | |
| WO | WO2008127415 A1 | 10/2008 | |
| WO | WO2008127978 A2 | 10/2008 | |
| WO | WO2008153732 A1 | 12/2008 | |
| WO | WO2009006622 A2 | 1/2009 | |
| WO | WO2009067486 A2 | 5/2009 | |
| WO | WO2009134888 A2 | 11/2009 | |
| WO | WO2009134896 A2 | 11/2009 | |
| WO | WO2010036864 A1 | 4/2010 | |

OTHER PUBLICATIONS

Humke; *Translaminar Screw Fixation in the Lumbar and Lumbosacral Spine: A 5-Year follow-up* Spine Journal. 1998; 23(10) pp. 1180-1184.

Shim; *Fluoroscopically Assisted Percutaneous Translaminar Facet Screw fixation following Anterior Lumbar Interbody Fusion*: Technical Report, Spine Journal 2005; 30(7) pp. 838-843.

Phillips; *Effect of Supplemental Translaminar Facet Screw Fixation on the Stability of Stand-Alone Anterior Lumbar Inter body fusion cages uner Physiologic Compressive Preloads*. Spine Journal, 2004; 29(16) pp. 1731-1736.

Eskander; *Analysis of Pedicle and Translaminar Facet Fixation in the multisegment Interbody Fusion Model*. Spine Journal, 2007; 32(7) pp. E230-E235.

Ferrara; *A Biomechanical Comparison of Facet Screw Fixation and Pedicle Screw Fixation*. Spine Journal 2003; 28(12). pp. 1226-1234.

Su; *An Anatomic and Radiographic Study of Lumbar Facets Relevant to Percutaneous Transfacet Fixation*. Spine Journal 2009; 34(11) pp. E384-E390.

Sasso; *Translaminar Facet Screw Fixation*. World Spine Journal. 2006; 1(1) pp. 34-39.

Depuy Acro Med, *Discovery Screw* System Surgical Technique. # IF16-20-000 Jun. 2003.

Depuy Spine Inc., *Discovery Screw System*. Product Webpage; Sep. 9, 2009.

Stonechipher; Thomas, MD. *Posterior Lumbar Interbody Fusion with Facet-Screw Fixation* Spine Volume; 14:4 1989. pp. 468-471.

Mahar; Andrew MS., *Biomechanical Comparison of a Novel Percutaneous Transfacet Device and a Traditional Posterior System for Single Level Fusion*. Spine Disorder Tech. vol. 19:8 Dec. 2006 pp. 590-594.

Medco Forum, *Percutaneous Lumbar Fixation Via PERPOS System From Interventional Spine*. vol. 14:49 pp. 1-2 Oct. 2007.

SpineFrontier, *Chameleon Facet Fuse*. Surgical Tech Brochure DOC#10035 Rev. A Oct. 15, 2009 pp. 1-46.

\* cited by examiner

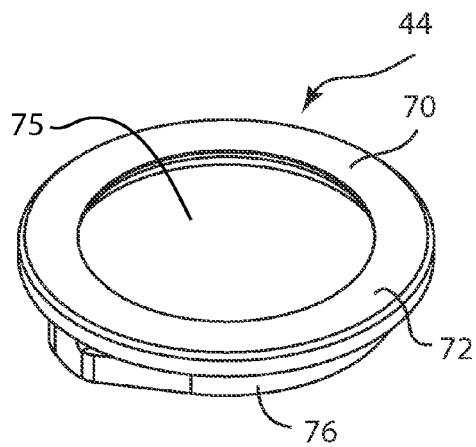
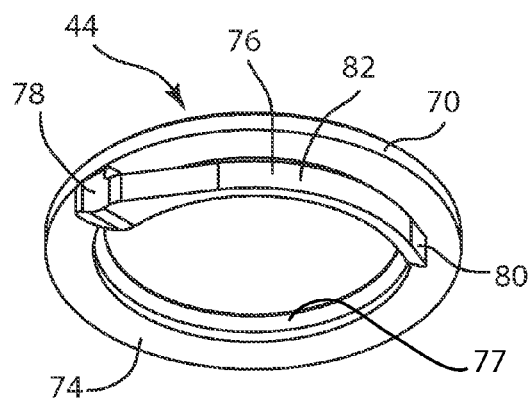
Fig. 3A
Fig. 3B
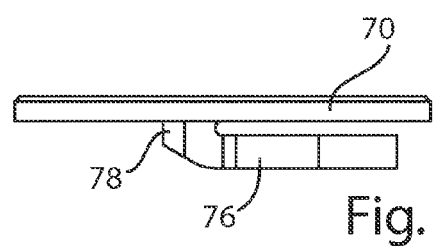
Fig. 3C
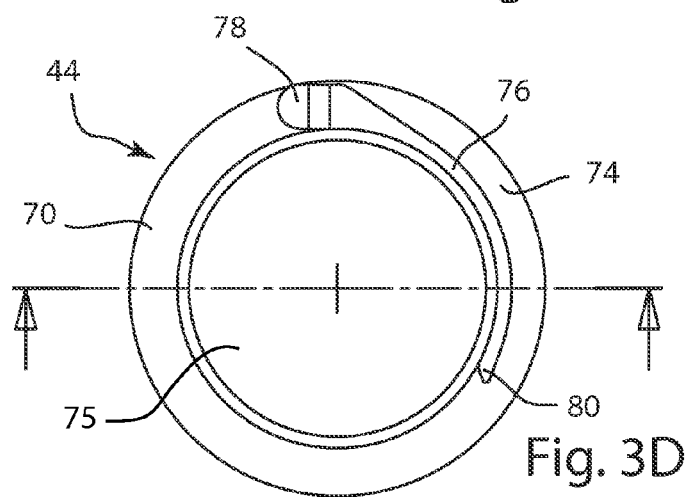
Fig. 3D
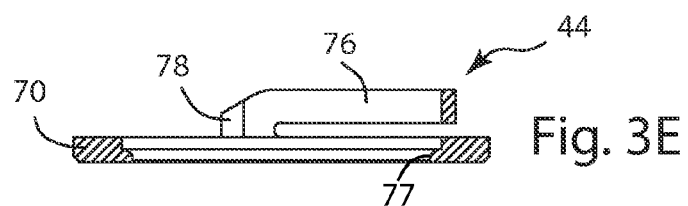
Fig. 3E

POLYAXIAL FACET FIXATION SCREW SYSTEM

CROSS-REFERENCE TO RELATED APPLICATIONS

This application claims the benefit of:

pending prior U.S. Provisional Patent Application No. 61/265,614 filed 1 Dec. 2009, which carries Applicants' docket no. OSM-2 PROV, and is entitled ANTI-BACK OUT POLYAXIAL FACET FIXATION SCREW SYSTEM; and pending prior U.S. Provisional Patent Application No. 61/374,862 filed 18 Aug. 2010, which carries Applicants' docket no. OSM-6 PROV, and is entitled CANNULA INSERTER.

The above-identified documents are incorporated herein by reference.

BACKGROUND

1. Technical Field

The present disclosure relates to orthopedic screw systems for bone fixation, and more particularly, to providing facet joint fixation screw systems with anti-backout features which prevent unintentional withdrawal of the screw.

2. The Relevant Technology

Loosening is a commonly encountered problem with screw fixation. A screw may work its way loose over time, such that fixation is compromised or the screw head protrudes to an undesirable extent from the surrounding material. Loosening is seen in orthopedic applications, such as facet joint fixation or facet joint fusion, at least partially because normal physiologic movement tends to encourage screw migration, and the bone into which the screw is driven tends to remodel over time. The three-dimensional topography of the bone surface presents an additional challenge in achieving secure fixation. The present disclosure provides a low-profile, self-contained, polyaxial, one-way screw and washer system that automatically and continuously resists any tendency of the screw to unthread from the surrounding material.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 3A illustrates a top perspective view of a cap of the washer assembly of FIG. 1A; FIG. 3B illustrates a bottom perspective view of the cap of FIG. 3A; FIG. 3C illustrates a side view of the cap of FIG. 3A; FIG. 3D illustrates a bottom view of the cap of FIG. 3A; FIG. 3E illustrates a side cross-sectional view of the cap of FIG. 3A;

DETAILED DESCRIPTION OF THE PREFERRED EMBODIMENTS

The present invention relates to systems and methods used in orthopedic surgery, and in particular, to facet joint fixation. Those of skill in the art will recognize that the systems and methods described herein may be readily adapted for other bone or joint fixation procedures. Those of skill in the art will also recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

Figure 1A:
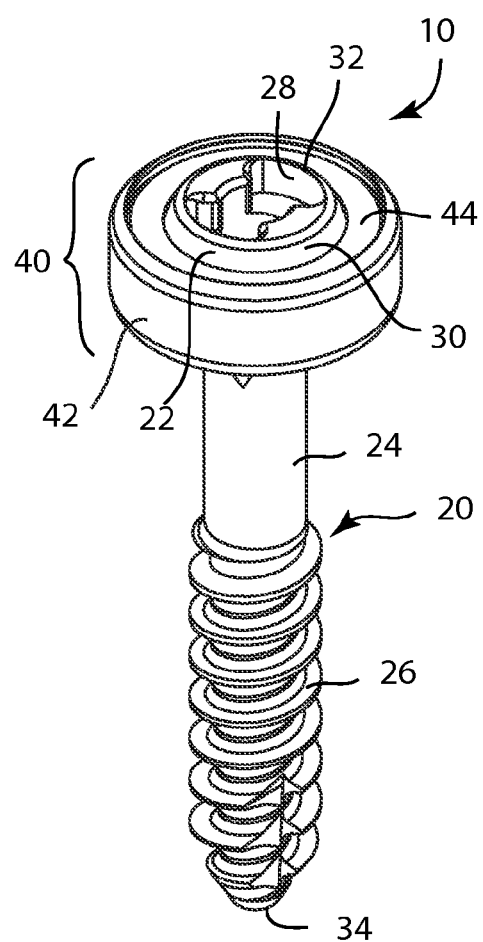
FIG. 1A illustrates a top perspective view of a system including a screw and a washer assembly.
Figure 1B:
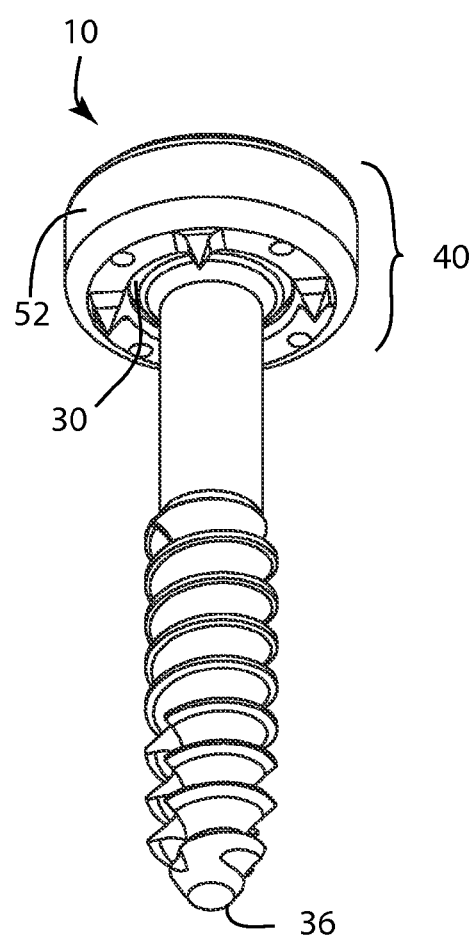
FIG. 1B is a bottom perspective view of the system of FIG. 1A.

Referring to FIGS. 1A and 1B, top and bottom perspective views illustrate a facet fixation screw system 10, comprising a screw 20 and a washer assembly 40. The washer assembly is captive to the head of the screw. The washer assembly includes an anti-backout mechanism which allows the screw to be freely rotated in one direction relative to the washer assembly, but binds the screw to the washer assembly when the screw is rotated in the opposite direction.

Screw 20 includes a spherical head 22 and a shaft 24. The shaft 24 includes a threaded portion 26 extending along a portion of the shaft. The entire length of the shaft may be threaded, or some portion or portions thereof. The thread pitch may be constant along the threaded portion, or may vary. Preferably, the shaft 24 includes a cannulation 25 to allow placement of the screw over a guidewire, but non-cannulated embodiments may also be provided. A drive feature 28 on the head 22 is shaped to cooperate with a driver instrument to facilitate placement, polyaxial adjustment and/or rotational driving of the screw. In the embodiment shown, the drive feature has a dogbone or bowtie shape; however other drive feature shapes are possible, including but not limited to: hexagon, pentagon, square, triangular, rectangular, cross, star, or other driver shapes known in the art. The drive feature 28 may be a recess as shown; in other embodiments the drive feature 28 may protrude to cooperate with a driver instrument having a complementary recessed driving feature. The head 22 further includes a spherical bearing surface 30. The screw 20 further includes a first end 32 which may be a proximal end, and at which the head 22 is located; and a second end 34 which may be a distal end, and at which a tip 36 of the shaft 24 is located.

Figure 4A:
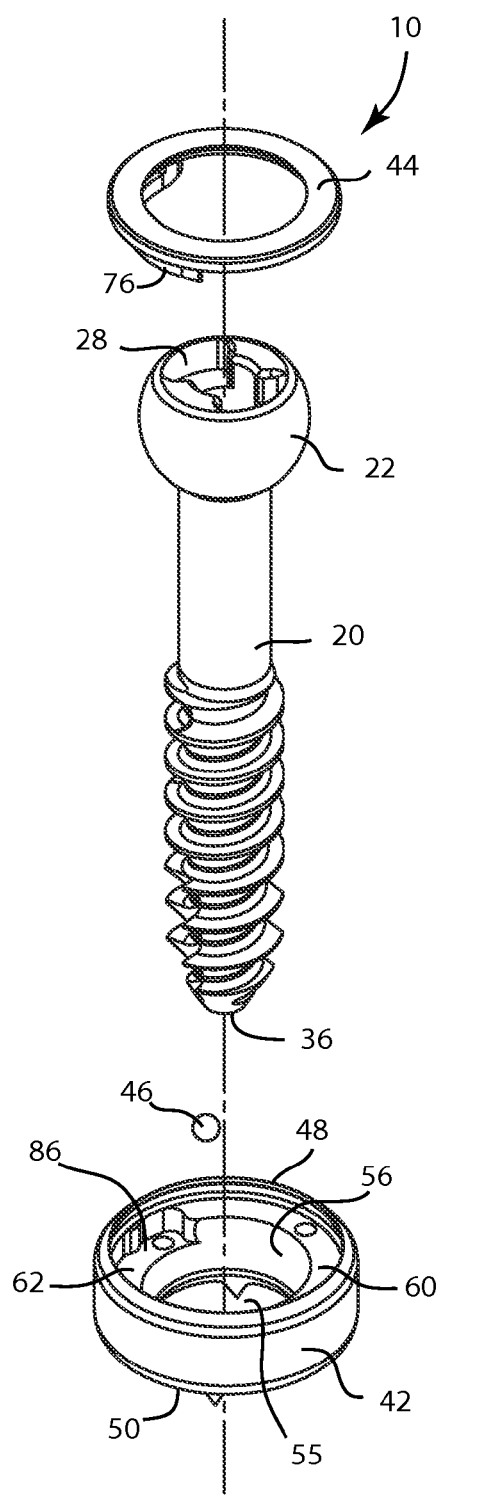
FIG. 4A illustrates a top perspective exploded view of the system of FIG. 1A.
Figure 4B:
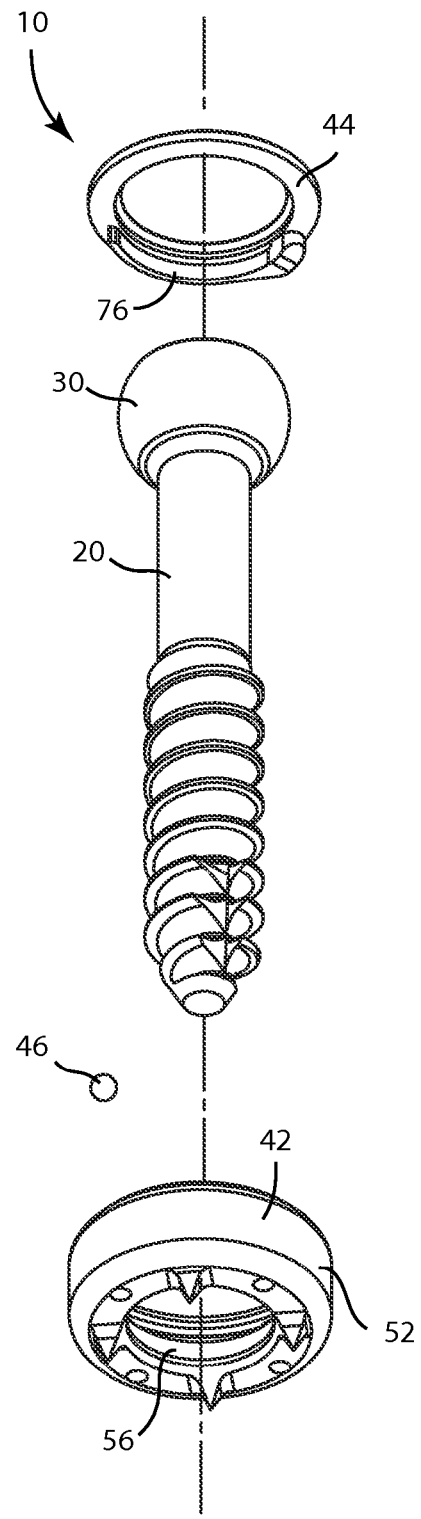
FIG. 4B illustrates a bottom perspective exploded view of the system of FIG. 1A.

Washer assembly 40 includes a washer 42 and cap 44. The washer assembly may further include a ball 46 (as best seen in FIGS. 4A and 4B) which is captured between the washer 42, the cap 44, and the head 22 when the washer assembly is operatively assembled with the screw 20 as in FIGS. 1A and 1B. The system 10 may be operatively assembled during manufacture and provided to the end users in the operatively assembled form, in sterile packaging.

Figure 2A:
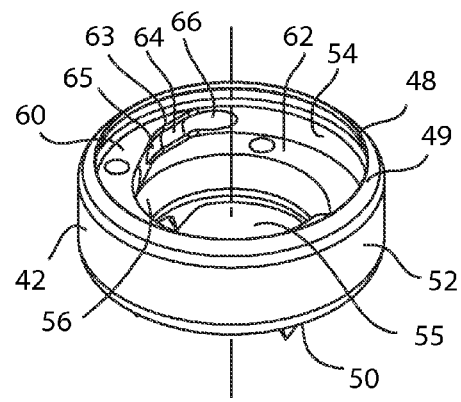
FIG. 2A illustrates a top perspective view of a washer of the washer assembly of FIG. 1A.
Figure 2B:
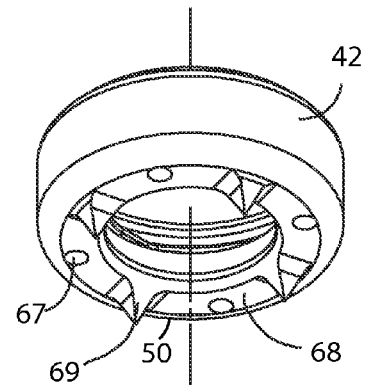
FIG. 2B illustrates a bottom perspective view of the washer of FIG. 2A.
Figure 2C:
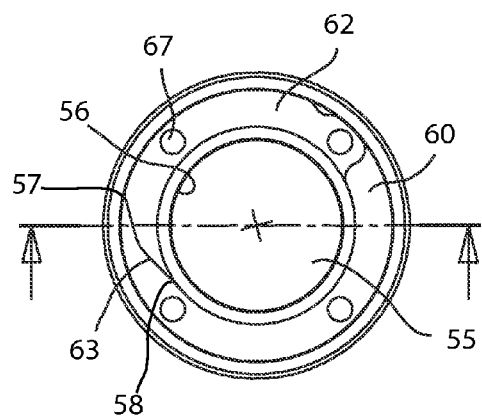
FIG. 2C illustrates a top view of the washer of FIG. 2A.
Figure 2D:
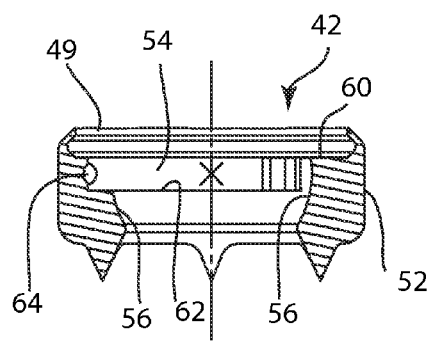
FIG. 2D illustrates a side cross-sectional view of the washer of FIG. 2A.

FIGS. 2A-2D show washer 42 in more detail. Washer 42 is annular, and has a first end 48 and a second end 50. First end 48 terminates with a relatively thin annular lip 49 which may project slightly toward the center of the washer 42. An outer peripheral wall 52 extends exteriorly between the first end 48 and the second end 50. An inner surface 54 extends interiorly between the first end 48 and the second end 50, forming a boundary to an aperture 55. An annular spherical recess 56 occupies a portion of the inner surface 54, and may form a socket to receive screw head 22. A portion of the annular spherical recess 56 is bounded toward the first end 48 by a first shelf 60, and the remainder is bounded toward the first end by a second shelf 62, which is recessed from, and may be described as lower than, the first shelf 60. Between the first shelf 60 and the second shelf 62, a portion of the inner surface 54 forms a ramp 63. The ramp 63 extends partially around the socket, or spherical recess 56, between a first end 57 which is outwardly displaced from the socket and a second end 58 which is tangential to the socket. Ramp 63 and second shelf 62 may be described as forming a tapered hole in the washer 42, with the first end 57 forming a wider part of the hole and the second end 58 forming a smaller end of the hole. An alcove 64 having a partial circular cross section is recessed into the inner surface 54; at least a portion of the alcove 64 overlaps the ramp 63, as seen in FIGS. 2A and 2D. Alcove 64 includes a first shallow portion 65 and a second deep portion 66, the depth of the alcove and the distance of the alcove from the spherical recess 56 increasing between the first and second portions. In this embodiment, alcove 64 has a cross section comprising an arc of a circle with a diameter which is complementary to the outer diameter of ball 46. The diameter of the circle may be slightly less than the outer diameter of ball 46, so that ball 46 is supported on the edges of alcove 64. Alcove 64 may be further described as a semicircular dished face, or a groove.

At least one bore 67 may extend longitudinally through the washer between the first end 48 and the second end 50, and may, for example, provide access for cleaning during or after manufacturing. The second end 50 of the washer 42 includes a bone engagement surface 68, at least a portion of which may be compressed against bone material when the screw system is implanted. At least one spike 69 protrudes from the second end 50. The spikes 69 may penetrate bone to provide additional fixation and/or rotation prevention. In other embodiments, pegs, nails, pins, keels or other bone-penetrating features may be included in place of or in addition to spikes 69, or no bone-penetrating features may be included. The bone engagement surface 68 may be roughened or porous to promote bone ongrowth or ingrowth; bone growth or other therapeutic agents may also be provided on the bone engagement surface 68.

Referring to FIGS. 3A-3E, the cap 44 includes a ring 70, the ring having a first side 72 and a second side 74 with an aperture 75 extending through the ring between the first and second sides 72, 74. A beam 76, which may be a cantilever beam, projects from the second side 74. A fixed end 78 of the beam is fixed to the ring, and a free end 80 is adjacent, but unconnected to, the ring 70. A beam body 82 extends between the fixed end 78 and the free end 80, is curved to follow the curvature of the ring 70, and may be parallel to the ring 70. The beam 76 may have the same radius of curvature as the ring 70, so that it extends along and overlaps a portion of the ring 70. The aperture 75 may include a lip 77 which has a diameter smaller than the equatorial diameter of the screw head 22.

Figure 5B:
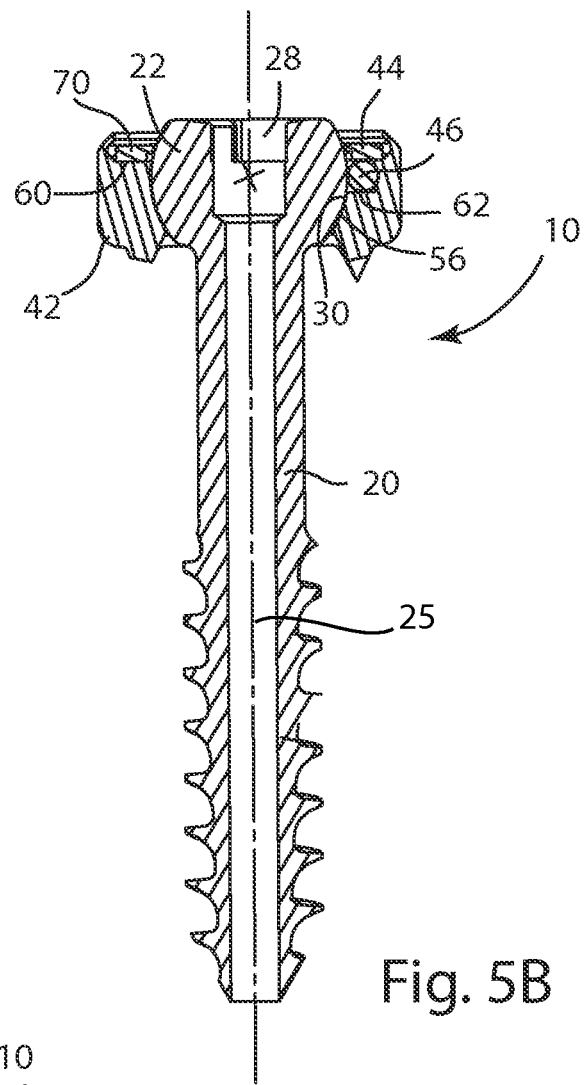
FIG. 5B illustrates a longitudinal cross-sectional view of the system of FIG. 5A.
Figure 5A:
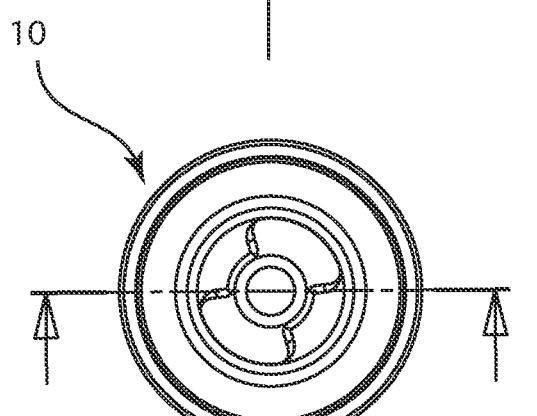
FIG. 5A illustrates a top view of the system of FIG. 1A.
Figure 6:
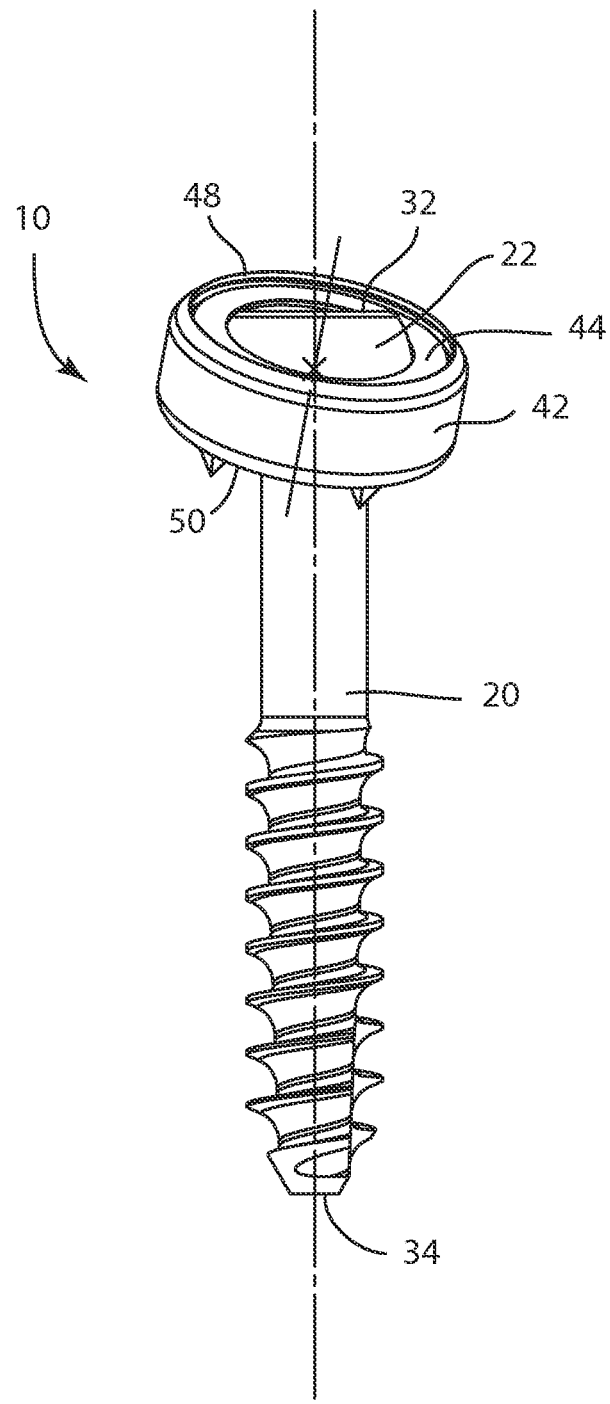
FIG. 6 illustrates a top perspective view of the system of FIG. 1A, showing the washer assembly polyaxially pivoted relative to the screw.
Figure 7A:
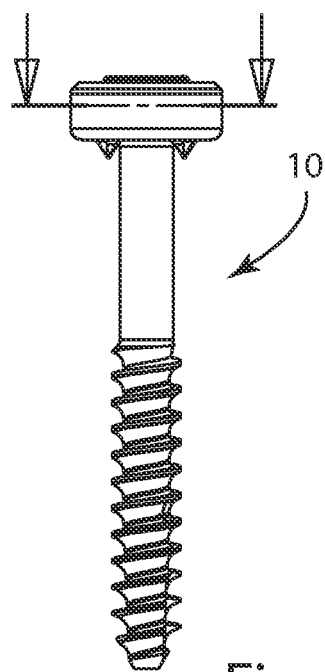
FIG. 7A illustrates a side view of the system of FIG. 1A.
Figure 7B:
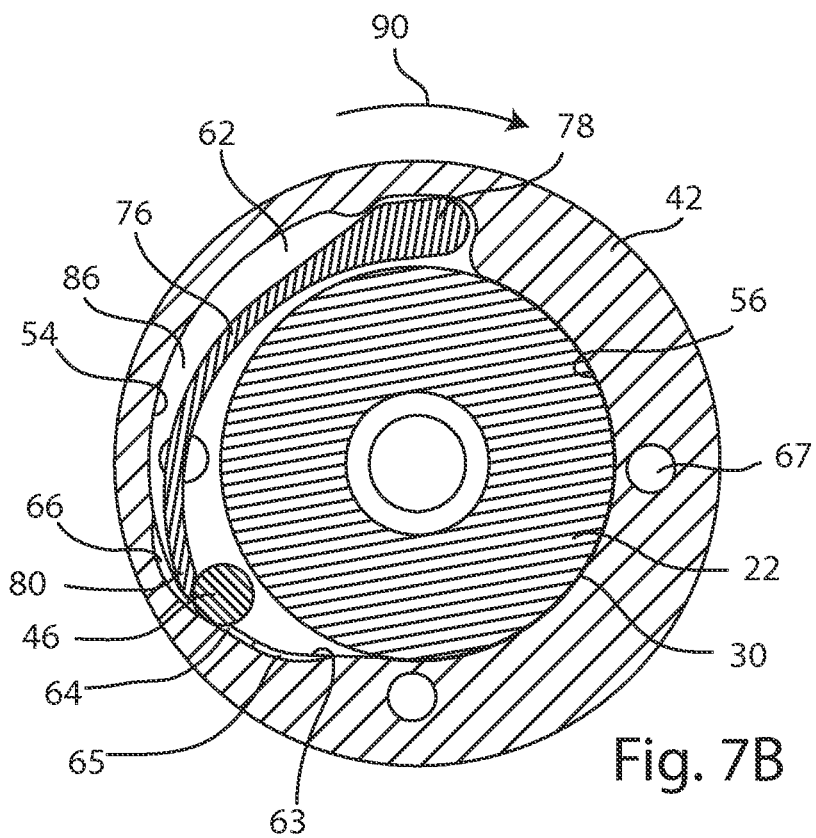
FIG. 7B illustrates a top cross-sectional view of the system of FIG. 7A with the system in an unlocked configuration in which the screw can rotate freely in a first direction relative to the washer assembly.
Figure 8A:
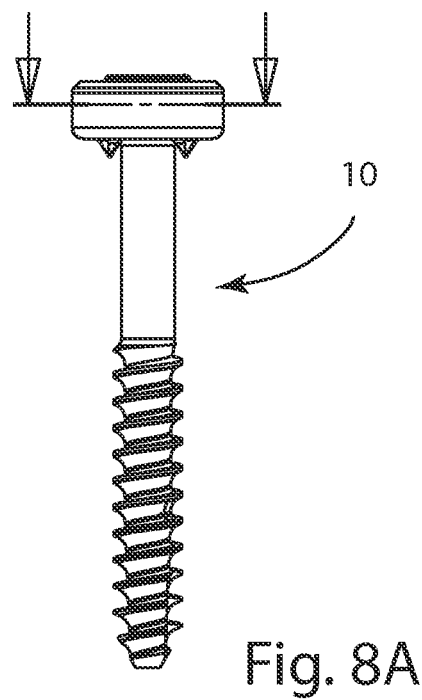
FIG. 8A illustrates a side view of the system of FIG. 1A.
Figure 8B:
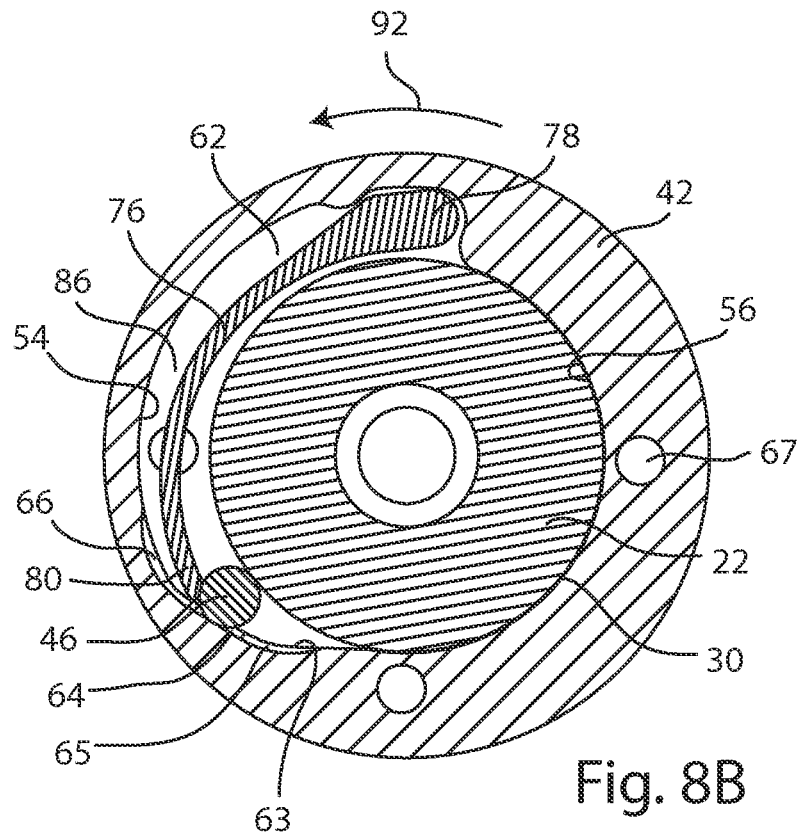
FIG. 8B illustrates a top cross-sectional view of the system of FIG. 8A with the system in a locked configuration in which the screw and washer assembly are frictionally locked together so that the screw is unable to rotate freely in a second direction relative to the washer assembly.

FIGS. 4A-4B depict screw system 10 in exploded views, and FIG. 5B is a cross-sectional view of the system in an operatively assembled configuration. When system 10 is assembled, screw 20 is received through washer 42, with tip 36 oriented in the same general direction as second end 50, and head 22 toward first end 48. Screw head 22 is retained by washer 42, with spherical bearing surface 30 bearing against annular spherical recess 56. Head 22 and washer 42 may thus form a ball and socket joint, with head 22 polyaxially pivotable relative to washer 42, as seen best in FIG. 6. Ball 46 is positioned inside washer 42 on second shelf 62, between head 22 and alcove 46. Cap 44 is positioned on washer 42, with a portion of ring 70 resting on first shelf 60. As best seen in FIGS. 7B and 8B, beam 76 extends from the second side 74 of the cap and is received in a gap 86 formed between head 22, second shelf 42, and inner surface 54 of washer 42. Free end 80 of beam 76 is adjacent alcove 64 of the washer, and ball 46 is between free end 80 and head 22. The free end 80 continuously spring biases the ball 46 toward the second end of the ramp 63. In other embodiments, ball 46 may be biased toward the second end of the ramp 63 by another kind of known spring, such as a spring clip, retaining ring, compression spring, extension spring, leaf spring, or torsion spring. In additional embodiments, ball 46 may be biased toward the second end of the ramp 63 by other known biasing means, such as magnetic bias, gravitational bias, or shape memory bias. Cap 44 is secured to washer 42 through a press-fit connection; as cap is pressed onto washer 42 in the described position, lip 49 of the washer may be deformed. In other embodiments, cap 44 may be secured to washer 42 by laser welding, a snap fit, a taper fit, a friction fit, threads, or any other known suitable connection means. It is appreciated that head 22 is polyaxially pivotable relative to washer 42 both before and after cap 44 is attached to washer 42.

Referring to FIGS. 7B and 8B, when screw system 10 is operatively assembled, screw 20 can rotate freely relative to washer assembly 40 in a first direction, but becomes rigidly locked to washer assembly 40 when rotated in a second direction. As shown in FIG. 7B, head 22 may be freely rotated in a first direction 90, which may be clockwise. As head 22 rotates, ball 46 is urged along alcove 64 in ramp 63, from shallow portion 65 toward deep portion 66. As ball 46 encounters free end 80 of beam 76, the beam is deflected toward deep portion 66, and the spring bias of the beam is temporarily overcome, allowing free rotation of the head 22. Although in FIG. 7B a small gap is shown between ball 46 and head 22, it is appreciated that ball 46 and head 22 may be in slight contact, yet head 22 is still able to freely rotate relative to washer 42.

As shown in FIG. 8B, rotation of head 22 in a second direction 92, which may be counterclockwise and opposite the first direction, causes a frictional lock to form between head 22 and washer assembly 40. As head 22 is rotated in the second direction 92, ball 46 is urged along alcove 64 in ramp 63 toward shallow end 65. Ball 46 is further urged toward shallow end 65 by the spring bias of beam 76. Ball 46 becomes jammed or wedged between alcove 64 and head 22, and may be deformed against head 22 as a result of the wedging action. In the present embodiment, ball 46 becomes wedged between two points of contact along the edges of alcove 64 and a single point of contact with head 22; the single point of contact may transform into a contact patch or area due to deformation of the ball 46 against the head 22. Further rotation of head 22 in the second direction is prevented; however washer 42 may still be polyaxially pivotable relative to head 22.

In one method of use, screw system 10 may be implanted across a facet joint to provide joint fixation, preventing articulation of the joint. A guidewire may be inserted across the joint, and a cannula inserted over the guidewire to the proximal facet. A cannula insertion instrument providing tissue dilation and cannula insertion, such as that disclosed in U.S. Provisional Patent Application No. 61/374,862, incorporated by reference into this disclosure, may be used to insert the cannula. The cannula may be temporarily docked to the proximal facet. The operatively assembled screw system 10 may be inserted through the cannula to the facet joint, with the screw first end 34 leading. A driver is used to rotate screw 20 in the first direction 90, driving screw 20 through the facets and across the joint. As screw 20 is driven, washer 42 comes in contact with the proximal facet, with at least a portion of bone engagement surface 68 in contact with the bony material of the facet. The polyaxial adjustability of the washer assembly relative to the screw allows the washer to sit at an angled position relative to the screw, which may be dictated by the surface topography of the facet and/or the surrounding environment. As screw 20 is driven further, spikes 69 may penetrate the surface of the facet, providing enhanced fixation and anti-rotation. When desired fixation of the joint and compression of the washer against the facet is achieved, rotation of screw 20 is ceased. Unintentional back-out and/or unintentional loosening of screw system 10 is prevented, as any rotation of screw 20 in second direction 92 results in locking together of screw 20 and washer assembly 40. Since washer assembly 40 is stabilized against the facet by spikes 69, screw 20 is effectively prevented from backing out or loosening.

Screw system 10 may be used in other applications in which two bone segments are fixed or compressed together to provide fixation or arthrodesis of a joint. The system may also be used in any orthopedic application in which anti-backout capabilities are desired, for example, to attach a prosthesis or implant to a bone. Non-limiting examples include attachment of articulating facet joint prostheses to vertebrae, attachment of intervertebral disk replacement prostheses, attachment of spinal rods, attachment of bone plates, and attachment of other joint prostheses, including knee, hip, shoulder, wrist, and/or ankle prostheses. Screw system 10 may also provide an anchor for anchoring of sutures, or natural or artificial tissues such as muscle, tendon, or ligament. One of skill in the art may appreciate that washer assembly 40, for example, may be modified by replacing washer 42 with an alternate component, which may include some or all of the features described above for washer 42.

The components of system 10 are preferably formed of titanium or titanium alloy. In other embodiments, system 10 or any of its component pails may comprise cobalt-chrome and its alloys, stainless-steel, titanium and its alloys, titanium carbide, titanium nitride, ion-implantation of titanium, diffusion hardened metals, diamond like coatings, diamond-like carbon, zirconium nitride, niobium, oxinium or oxidized zirconium, ceramics such as alumina and zirconia, polymers, or other biocompatible materials. Any part may comprise a combination of any of the materials listed, and the system 10 may comprise parts made of differing materials.

Any of the components disclosed herein may include surface treatments or additives in one or more of the component materials to provide beneficial effects such as anti-microbial, analgesic or anti-inflammatory properties. Any of the components disclosed herein may include coatings or treatments to provide surface roughening, including but not limited to knurling or porous coating, among others. Such treatments may be directionally applied to promote movement between component parts in one direction, and/or increase friction between component parts in another direction.

The present invention may be embodied in other specific forms without departing from its spirit or essential characteristics. It is appreciated that various features of the above described examples and embodiments may be mixed and matched to form a variety of other combinations and alternatives. It is also appreciated that this system should not be limited simply to facet joint fixation. As such, the described embodiments are to be considered in all respects only as illustrative and not restrictive. The scope or the invention is, therefore, indicated by the appended claims rather than by the foregoing description. All changes which come within the meaning and range of equivalency of the claims are to be embraced within their scope.

The invention claimed is:

1. A system, comprising:
a screw, wherein the screw comprises a spherical head; and
a washer assembly around the head, wherein the washer assembly comprises:
a washer, wherein the washer comprises a socket and a ramp, wherein the socket receives the head to form a ball-and-socket joint, wherein the ramp extends partially around the socket between a first end which is outwardly displaced from the socket and a second end which is tangential to the socket, and wherein the ramp comprises a semicircularly dished face,
a cap secured to the washer, wherein the cap comprises a ring, wherein an inner diameter of the ring is smaller than an equatorial diameter of the spherical head, and wherein the spherical head is interposed between the ring and the socket, and
a ball, wherein the ball is positioned between the face and the head, wherein rotation of the head in a first direction urges the ball along the face toward the first end so that the ball fits loosely between the face and the head so that the screw is freely rotatable relative to the washer assembly, wherein rotation of the head in a second direction urges the ball along the face toward the second end until the ball binds between the face and the head so that the screw and the washer assembly are locked together, wherein the second direction is opposite the first direction.

2. The system of claim 1, wherein the washer assembly is captive to the head.

3. The system of claim 1, wherein the ball is continuously biased toward the second end, wherein rotation of the head in the first direction temporarily overcomes the bias to urge the ball toward the first end.

4. The system of claim 1, wherein, when the ball binds between the face and the head, the ball deforms against the head.

5. The system of claim 1, wherein the cap comprises:
a cantilever beam, wherein the beam extends between a fixed end of the beam and a free end of the beam, wherein the fixed end is connected to the ring, wherein the free end continuously spring biases the ball toward the second end, wherein rotation of the head in the first direction deflects the beam to temporarily overcome the bias.

6. The system of claim 1, wherein the screw comprises a shaft extending from the head through the washer assembly, wherein the washer assembly comprises a spike pointing along the shaft away from the head.

7. A system, comprising:
a screw, wherein the screw comprises a spherical head; and
a washer assembly captive to the head, wherein the washer assembly comprises:
- a washer, wherein the washer comprises a socket and a ramp, wherein the socket receives the head, wherein the ramp extends between a first end which is outwardly displaced from the socket and a second end which is tangential to the socket, and wherein the ramp comprises a semicircularly dished face,
- a cap secured to the washer, wherein the cap comprises a ring, wherein an inner diameter of the ring is smaller than an equatorial diameter of the head, and wherein the head is interposed between the ring and the socket, and
- a ball positioned between the face and the head, wherein rotation of the head in a first direction urges the ball along the face toward the first end so that the ball fits loosely between the face and the head, wherein rotation of the head in a second direction urges the ball along the face toward the second end until the ball binds between the face and the head so that the screw and the washer assembly are locked together, and wherein the second direction is opposite the first direction.

8. The system of claim 7, wherein the socket is spherical, wherein the socket is complementary to the head.

9. The system of claim 7, wherein the ball is continuously biased toward the second end, wherein rotation of the head in the first direction temporarily overcomes the bias to urge the ball toward the first end.

10. The system of claim 7, wherein, when the ball binds between the face and the head, the ball deforms against the head.

11. The system of claim 7, wherein the cap comprises:
a cantilever beam, wherein the beam extends between a fixed end of the beam and a free end of the beam, wherein the fixed end is connected to the ring, wherein the free end continuously biases the ball toward the second end, wherein rotation of the head in the first direction deflects the beam to temporarily overcome the bias.

12. The system of claim 7, wherein the screw comprises a shaft extending from the head through the washer assembly, wherein the washer assembly comprises a spike pointing along the shaft away from the head.

13. A system, comprising:
a screw, wherein the screw comprises a spherical head;
a washer encircling the head, wherein the washer comprises an aperture extending through the washer from a first side of the washer to a second side of the washer opposite the first side, wherein the head is positioned within the aperture, wherein the washer comprises a side wall encircling the aperture, wherein the side wall comprises a groove extending at least partially around the side wall, wherein the groove extends between a shallow end of the groove and a deep end of the groove;
a cap secured to the washer, wherein the cap comprises a ring, wherein an inner diameter of the ring is smaller than an equatorial diameter of the head, wherein the head is interposed between the ring and the aperture; and
a ball positioned between the side wall and the head, wherein the ball travels along the groove in response to rotation of the head relative to the washer;
wherein, when the head rotates in a first direction, the ball travels along the groove to the deep end where the ball is loose between the deep end and the head so that the head rotates freely relative to the washer;
wherein, when the head rotates in a second direction opposite the first direction, the ball travels along the groove to the shallow end where the ball jams between the shallow end and the head so that the screw, washer, and ball are frictionally locked together.

14. The system of claim 13, wherein the washer is captive to the head.

15. The system of claim 13, wherein the aperture comprises a spherical socket complementary to the head, wherein the washer is polyaxially pivotable about the head.

16. The system of claim 13, wherein the ball is continuously biased toward the shallow end, wherein rotation of the head in the first direction temporarily overcomes the bias to urge the ball toward the deep end.

17. The system of claim 13, wherein, when the ball jams between the shallow end and the head, the ball deforms against the head.

18. The system of claim 13, wherein the cap comprises:
a cantilever beam, wherein the beam extends between a fixed end of the beam and a free end of the beam, wherein the fixed end is connected to the ring, wherein the free end continuously biases the ball toward the shallow end, wherein rotation of the head in the first direction deflects the beam to temporarily overcome the bias.

19. The system of claim 13, wherein the screw comprises a shaft extending from the head through the washer, wherein the washer comprises a spike pointing along the shaft away from the head.

20. A system, comprising:
a screw, wherein the screw comprises a head;
a washer assembly encircling at least a portion of the head, wherein the washer assembly comprises:
a washer body encircling at least a portion of the head,
a ring encircling at least a portion of the head,
a tapered surface with a cross section comprising an arc of a circle, and
a sphere, wherein the sphere is between the head and at least a portion of the washer body, wherein the sphere is interposed between the ring and the washer body,
wherein, when the ring rotates relative to the head, the sphere moves along the tapered surface between a first position and a second position;
wherein the washer body is locked to the head when the sphere is in the first position;
wherein the washer body is unlocked and freely polyaxially rotatable relative to the head when the sphere is in the second position;
wherein the washer body locks and unlocks in response to movement of the sphere along the tapered surface.

21. The system of claim 20, wherein, when the ring rotates relative to the head in a first direction, the sphere moves along the tapered surface toward the first position;
wherein, when the ring rotates relative to the head in a second direction, the sphere moves along the tapered surface toward the second position, wherein the second direction is opposite the first direction;
wherein the sphere is wedged against the washer body when the sphere is in the first position; and
wherein the washer assembly is captive to the head.

22. A system, comprising:
a screw, wherein the screw comprises a spherical head; and
a washer assembly around the head, wherein the washer assembly comprises:

a washer, wherein the washer comprises a socket and a ramp, wherein the socket receives the head to form a ball-and-socket joint, wherein the ramp extends partially around the socket between a first end which is outwardly displaced from the socket and a second end which is tangential to the socket and wherein the ramp comprises a semicircularly dished face, a cap, wherein the cap comprises a ring and a cantilever beam, wherein the ring is secured to the washer, wherein the beam extends between a fixed end of the beam and a free end of the beam, and wherein the fixed end is connected to the ring; and a ball, wherein the ball is positioned between the face and the head, wherein rotation of the head in a first direction urges the ball along the face toward the first end so that the ball fits loosely between the face and the head so that the screw is freely rotatable relative to the washer assembly, wherein rotation of the head in a second direction urges the ball along the face toward the second end until the ball binds between the face and the head so that the screw and the washer assembly are locked together, wherein the second direction is opposite the first direction, wherein the free end continuously spring biases the ball toward the second end, and wherein rotation of the head in the first direction deflects the beam to temporarily overcome the bias.

* * * * *